United States Patent [19]

Shattuck

[11] Patent Number: 4,622,034

[45] Date of Patent: Nov. 11, 1986

[54] MEDICAL TUBE HOLDER

[75] Inventor: Bruce T. Shattuck, San Antonio, Tex.

[73] Assignee: Kinetic Concepts, Inc., San Antonio, Tex.

[21] Appl. No.: 705,985

[22] Filed: Feb. 27, 1985

[51] Int. Cl.4 ............................................. A61M 25/02
[52] U.S. Cl. ............................ 604/179; 128/207.17; 128/DIG. 26
[58] Field of Search ............................ 604/174–180; 128/207.17, 207.18, 133, DIG. 26

[56] References Cited

U.S. PATENT DOCUMENTS

| | | | |
|---|---|---|---|
| 3,688,774 | 9/1972 | Akiyama | 128/207.17 |
| 3,774,616 | 11/1973 | White et al. | 128/207.17 |
| 3,927,676 | 12/1975 | Schultz | 128/207.17 |
| 3,946,742 | 3/1976 | Eross | 128/207.17 |
| 4,088,136 | 5/1978 | Hasslinger et al. | 604/179 |
| 4,313,437 | 2/1982 | Martin | 128/207.17 |
| 4,326,515 | 4/1982 | Shaffer et al. | 128/207.17 |
| 4,367,735 | 1/1983 | Dali | 128/207.17 X |
| 4,520,813 | 6/1985 | Young | 604/179 |

Primary Examiner—Dalton L. Truluck
Attorney, Agent, or Firm—Cox & Smith Inc.

[57] ABSTRACT

A tube holder comprised of a foam strip which has apertures in the strip running the length of the strip at spaced intervals. The resilient nature of the foam facilitates holding a trachea or nasogastric tube sufficiently firmly in place when the strip is wrapped around the patient's head and two of the apertures are aligned so that the tube can be inserted through the apertures into a patient's body orifice. The apertures may be circular or slits. An alternative embodiment uses a similar foam material but has a single aperture at one end for inserting the tube through, with the other end of the strip wrapping around a person's head and being wrapped around the tube and fixed by Velcro or similar substances.

7 Claims, 6 Drawing Figures

MEDICAL TUBE HOLDER

BACKGROUND OF THE INVENTION

The present invention relates to a device for holding medical tubes at a fixed place on a patient's body. More particularly, the present invention may be used to wrap around the head of a person for use as a tube holder.

A trachea or nasogastric tube holder is a device well known in the art. However, presently available tube holders have limitations and disadvantages, either from the perspective of the patient or from the perspective of the physician.

A trachea tube is a tube used in the medical arts to insure that air is able to clear the mouth of a patient and enter the throat passageway, to allow the patient to breath. The tube may be inserted into the mouth until it rests at the back of the throat in or near the esophagus in order to avoid any possibility of an obstruction cutting off breathing. Nasogastric tubes perform the same function through the nose and are also commonly used in operations and in patient care. Once inserted, the tube needs to be held in place firmly so that it will not be dislodged. One source of dislodging is when the patient does so unintentionally, by moving, coughing, etc. The device holding the tube should be as comfortable as possible for the benefit of the patient.

Traditionally, the tubes have been held in place simply by taping them with one of the varieties of medical tape well known in the art. This method may be unsatisfactory because the patient's face must be used as an anchor for the tape and the tape's sticky surface can cause discomfort. Also, oil or liquids on the skin surface may cause the tape to lose its grip on the patient's skin. Some current tube holders do not employ a taping concept but are large, bulky, expensive, or too uncomfortable for the patient.

One of the devices which has attempted to overcome this problem is that disclosed by Schultz (U.S. Pat. No. 3,927,676). This device discloses an adhesive tape with a non-adhesive backing. The backing is placed against the skin of the patient so that there is no sticky substance to put on the patient's skin. The tape is split, lengthwise, near the ends, so that when a portion of the non-adhesive backing is peeled off, the split ends can be adhered around the trachea tube. This device has a disadvantage because it still has to employ an adhesive substance, which may require replacement occasionally as it loses its adhesiveness. Also, it is difficult to use, compared to the present invention, as the nurse or physician must be certain that the proper side of the tape is facing the tube, peel off the backing, separate the split ends, and wrap them around the trachea tube. Finally, this device is not easily adaptable to all types of patients, as the split ends must be close enough to the end so that the tape maintains its structrual integrity, which necessitates that the tape be manufactured in a variety of lengths to allow for use with patients ranging from infants to adults.

Another known tube holding device includes tape or VELCRO fasteners for connecting to a tube or cannula with the portion which wraps around the rear of the patient's head having a cushioning means for added comfort to the patient. This device may be unsatisfactory for holding trachea tubes, because it may not maintain a tube directly over the patient's mouth, allowing the tube to be pinched or pressed against the bottom of the mouth, and in one version uses adhesive for fixing the device, which has the disadvantages mentioned above.

Cost, ease of storage, and ease of packaging are other important considerations in the manufacture of tube holding devices. In order to contain costs, it is normally the case that if the tube holding device and the portion of the device which secures the tube holding device to the body are the same, then the cost of manufacture will be lower, assuming the cost of materials to be approximately the same. Also, it may be desirable to provide a device which can be easily packaged in a variety of ways. For example, if sterility is a consideration, then it may be desirable to manufacture the device in preselected lengths and wrapped in sterile packaging. However, if sterility is not a consideration, it would be advantageous if the devices could be packaged en masse and cut to the desired length when installed. Devices which may suffer from these limitations are disclosed by Eross (U.S. Pat. No. 3,946,742), White, et al (U.S. Pat. No. 3,774,626) and Akiyama (U.S. Pat. No. 3,688,774). The device disclosed by Eross provides for multiple securing straps and a separate tube holder, which may increase production costs and requiring packaging as single entities. The device disclosed by White, et al similarly provides for a separate tube holder of relatively complicated design, so that it may also be more expensive to manufacture and less flexible to package. Finally, the device disclosed by Akiyama has separate restraining and tube holding devices, with the possible consequence of increased cost and being less amiable to mass packaging.

The present invention seeks to overcome these preceding difficulties of the prior art and provides a cheaper, simpler, and more comfortable device for holding tubes.

Therefore, it is an object of the present invention to provide a tube holder which effectively holds a tube in place so that it cannot easily be dislodged. Further, it is an object of the present invention to have a tube holder which is simple to put in place. Also, it is an object of the present invention to have a tube holder which does not require adhesives or tape for connecting the holder, but if adhesives are used they should not adhere directly to the skin. Also, it is an object of the present invention to provide a tube holder which is comfortable to patients. Also, it is an object of the present invention to have a tube holder which has a longer useful life. Also, it is an object of the present invention to provide a tube holder which can be used on patients of any size, and, if necessary, trimmed accordingly. Finally, it is an object of the present invention to provide a tube holder which can be made sterile and disposable. Other objects will become evident as the invention is further described.

SUMMARY OF THE INVENTION

A medical tube holder comprising a flexible strip of resilient foam material having at least two apertures at spaced intervals along the length of the strip. The tube holder can be placed around a patient's head with the medical tube(s) inserted through the apertures so the holder holds the tube(s) in place. Another embodiment has at least one aperture relatively near one end of the foam strip for receiving a medical tube, with the other end of the foam strip being wrapped around the patient's head and being fixed around the tube adhesively.

DESCRIPTION OF THE PREFERRED EMBODIMENTS

Figure 1:
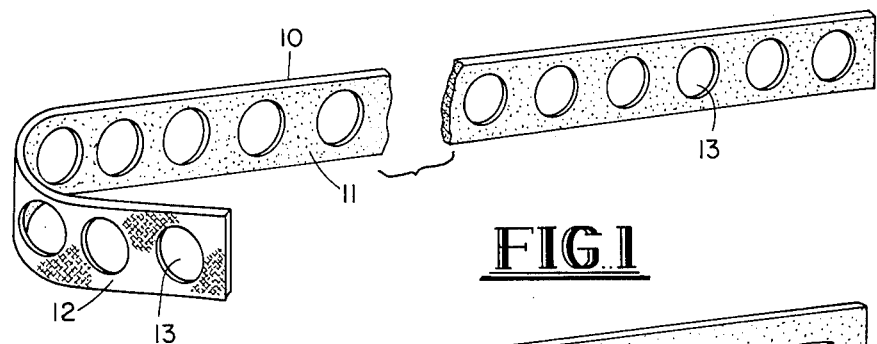
FIG. 1 is a side perspective view of one embodiment of the invention.
Figure 3:
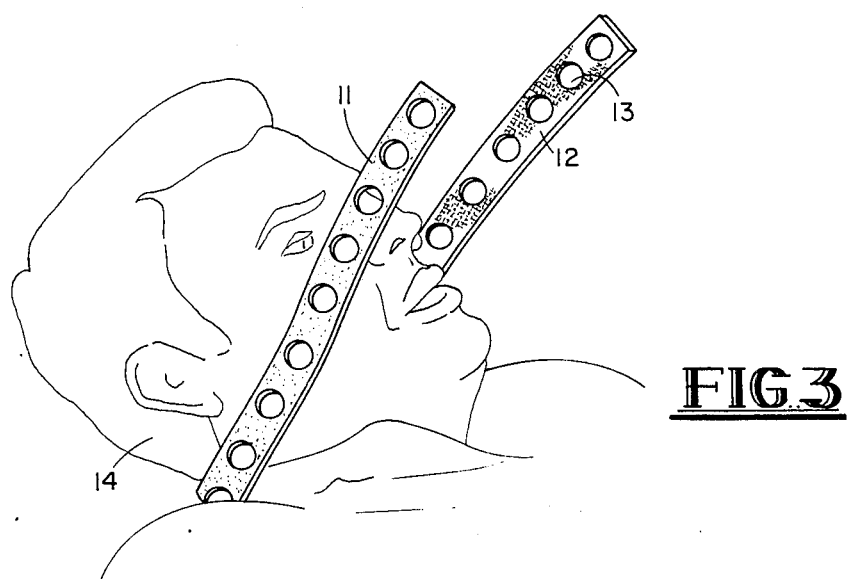
FIG. 3 is a side perspective view of the first embodiment of the invention in preparation for installation.
Figure 4:
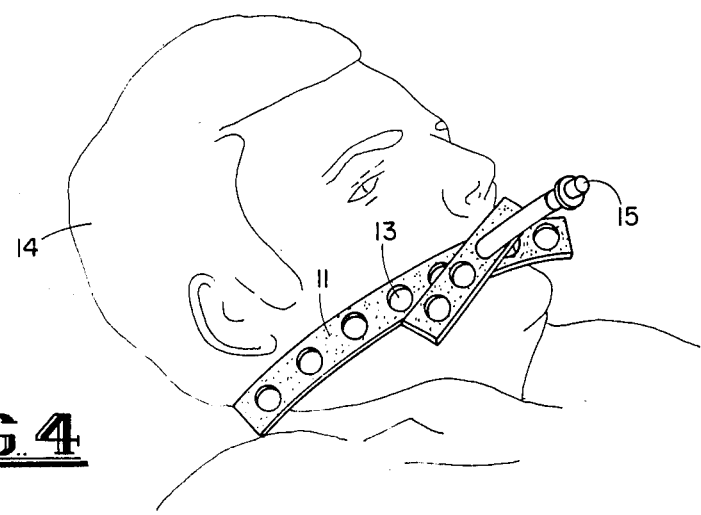
FIG. 4 is a side perspective view of the first embodiment of the invention, as installed.

Referring now to FIG. 1, a first embodiment is shown. The tube holder (or "device"), referred to generally at reference numeral 10, is a strip of foam material approximately one inch wide and approximately one third of an inch thick. A laminated combination of polyether foam and cotton-vel mesh is contemplated as the material to be used. These materials are manufactured by Foam Tech, although other materials with sufficient flexibility, resiliency and cushioning qualities could be used. The strip is preferably made of material which can be made sterile. The device has a porous side 11 and a smooth side 12. The smooth side 12 is smoother because it may be comprised of the cotton-vel mesh, a fabric-like material. The mesh is laminated or adhered as a backing onto the polyether foam which forms the porous side 11 of the device. The smooth side 12 is turned toward the patient's skin, as shown in FIG. 3, because it is less scratchy or irritating and more comfortable for the patient. The porous side 11 is turned away from the patient's skin in order to better grip the overlapping portion of the device and prevent slippage of the tube as shown in FIG. 4. Also, the smooth side 12 acts as a reinforcement backing to the polyether foam material of the porous side 11 and prevents the apertures, to be described later, from tearing too easily.

In one embodiment, circular apertures 13 are cut at substantially regular intervals in the center of the holder 10, lengthwise. The circular apertures 13 may be approximately one-half inch in diameter. The apertures need not be cut along the entire length of the holder 10 as long as they are located near the ends for holding a tube.

As shown in FIGS. 3 and 4, to install the tube holder 10, the holder 10 is wrapped around the patient's head 14 with the smooth side 12 facing the skin. The holder 10 is overlapped like a belt and adjusted according to the size of the neck and head of the patient. The holder 10 is adjusted to a snug but comfortable position, with the circular apertures 13 from the bottom and top ends of the holder 10 being aligned. The tube 15 is then inserted through the two aligned circular apertures 13 into the patient's mouth or other orifice. Because of the resilient nature of the material used in the device, the sides of the circular apertures 13 may engage the tube 15 firmly enough to prevent an accidental dislodging of the tube. Also, the smooth side 12 of the holder 10 will releasably engage the patient's skin sufficiently to prevent sideways movement of the holder 10. The cushioned properties provide greater comfort to the patient who is using the tube.

Figure 2:
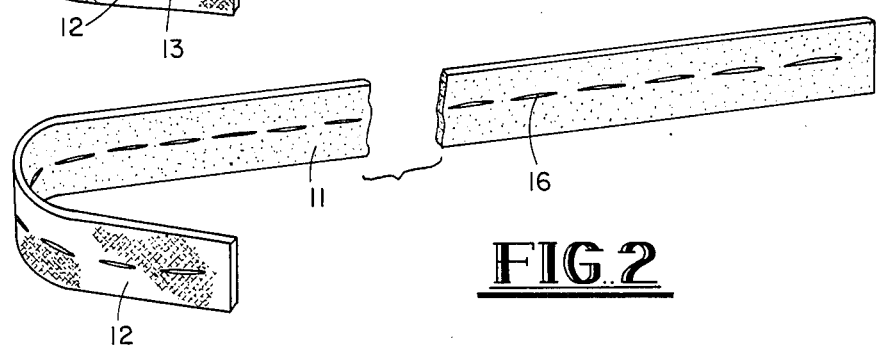
FIG. 2 is a side perspective view of a second embodiment of the invention.

Another embodiment of the invention is shown in FIG. 2. The same foam materials of approximately the same length are used in this embodiment, also. Instead of circular apertures 13 being cut in the holder 10 lengthwise at regular intervals, slit apertures 16 are cut in the holder 10 lengthwise, at regular intervals. Again, the holder 10 is wrapped around the patient's head 14 and two of the overlapping slit apertures 16 are aligned. The tube 15 is inserted through the slit apertures 16 and is held in place by the contact with the sides of the slit aperture 16.

Because the apertures of the first embodiment are circular in nature, the first embodiment can engage substantially larger tubes than the second embodiment. However, the first embodiment is limited in that the tube 15 should be at least as large as or larger than the circular aperture 13 to allow the resilient foam to engage the tube 15 sufficiently to hold it in place and prevent accidental dislodging of the tube 15.

The embodiments of FIGS. 1-4 may be manufactured as continuous strips and cut in strips for use. However, in order to maintain them in a sterile condition they may be packaged in pre-cut lengths in sterile packages and excess length cut off when used.

Figure 5:
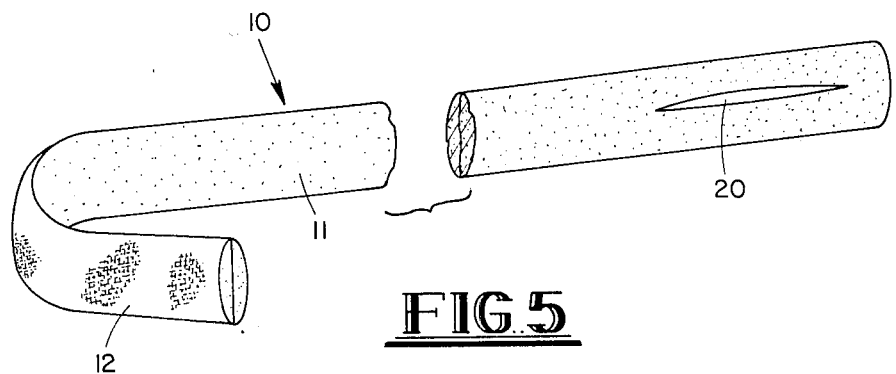
FIG. 5 is a side perspective view of a third embodiment of the invention.
Figure 6:
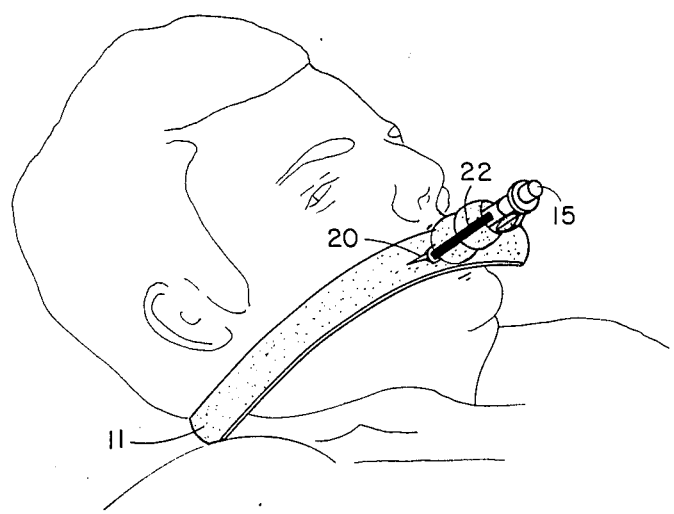
FIG. 6 is a side perspective view of a third embodiment of the invention, as installed.

A third embodiment is shown in FIG. 5. This embodiment also uses a foam material, except that this embodiment uses a polyester foam manufactured by Scott Paper Company for the porous side 11, and a brush nylon tricot for the smooth side 12. Again the two strips are laminated into a single piece. Instead of a number of regularly spaced apertures 13, the embodiment contains a single, relatively long aperture 20 near one end of the holder 10. The aperture 20 of this embodiment is approximately two inches long, although it may be varied as appropriate. The holder 10 is shown installed in FIG. 6, where the aperture 20 is placed over the lips (not shown), smooth side 12 toward the skin. A tube 15 is then inserted through the aperture 20, although the aperture 20 may be slid down over the tube 15 if the tube 15 is already in place. The device is then wrapped around the head (not numbered) of a patient, across the cheek and lower lip, and then wrapped around the tube 15. The device secures the tube 15 by a bonding substance 22, known in the art. Tape may be applied to the holder 10 and to the tube 15 as the bonding substance 22 as long as it does not touch the patient, but Applicant uses a VELCRO bonding substance 22 in the present embodiment, the VELCRO holding the device firmly around the tube 15 by joining the coils of the device together, as shown in FIG. 6.

Although the invention has been described in conjunction with the foregoing embodiments, a great number of variations, alternatives and modifications will be apparent from the concept of the present invention to those of ordinary skill in the art.

I claim:

1. A medical tube holding device comprising:
   a flexible strip of resilient foam material;
   a flexible strip of porous material coextensive with said flexible foam strip having a surface smoother than the surface of said strip of foam material and integral therewith; and
   a plurality of holes spaced along the length of said integral foam and porous material strip.

2. The medical tube holding device of claim 1 wherein each of the holes in said integral foam and porous material strip is circular.

3. The medical tube holding device of claim 1 wherein each of the holes in said integral foam and porous material strip is a slit.

4. A medical tube holding device comprising:
an elongate flexible strip of resilient foam material;
a flexible strip of porous material coextensive with said flexible foam strip having a surface smoother than the surface of said strip of foam material and integral therewith;
means for releasably securing one end of said integral foam and porous material strip to the other end of said strip; and
aperture means extending through said strip for receiving a medical tube near the other end of said integral foam and porous material strip, the medical tube receiving means at said other end of said integral foam and porous material strip being operable to secure a medical tube in place in cooperation with the means for releasably securing the other end of said integral foam and porous material strip when said aperture means and said means for releasably securing the other end of said integral foam and porous material strip are in alignment.

5. The medical tube holding device of claim 4 wherein said aperture means is circular.

6. The medical tube holding device of claim 4 wherein said aperture means is a slit.

7. The medical tube holding device of claim 4 wherein said medical tube receiving means comprises a plurality of holes spaced along the length of said strip.

* * * * *